(12) United States Patent
Schraga

(10) Patent No.: US 10,118,000 B2
(45) Date of Patent: Nov. 6, 2018

(54) PEN NEEDLE INSTALLATION AND REMOVAL SAFETY COVER AND PEN NEEDLE ASSEMBLY UTILIZING THE SAME

(71) Applicant: STAT MEDICAL DEVICES, INC., N. Miami Beach, FL (US)

(72) Inventor: Steven Schraga, Surfside, FL (US)

(73) Assignee: STAT MEDICAL DEVICES, INC., North Miami, FL (US)

( * ) Notice: Subject to any disclaimer, the term of this patent is extended or adjusted under 35 U.S.C. 154(b) by 0 days.

(21) Appl. No.: 14/689,500

(22) Filed: Apr. 17, 2015

(65) Prior Publication Data

US 2015/0297837 A1    Oct. 22, 2015

Related U.S. Application Data

(60) Provisional application No. 61/982,030, filed on Apr. 21, 2014.

(51) Int. Cl.
*A61M 5/32* (2006.01)
*A61M 5/00* (2006.01)
*A61M 5/34* (2006.01)

(52) U.S. Cl.
CPC .......... *A61M 5/3202* (2013.01); *A61M 5/002* (2013.01); *A61M 5/3293* (2013.01);
(Continued)

(58) Field of Classification Search
CPC .. A61M 5/3202; A61M 5/002; A61M 5/3293; A61M 5/34; A61M 5/3205; A61M 2005/3206; A61M 5/3213; A61M 5/343; B65D 39/08; B65D 39/088; B65D 41/0464; B65D 41/04; B65D 47/122; B65D 47/143; B65D 45/325; B65D 45/322; A61J 1/1418; A61J 1/1412
See application file for complete search history.

(56) References Cited

U.S. PATENT DOCUMENTS 4,894,055 A    1/1990 Sudnak
4,909,792 A    3/1990 Norelli
(Continued)

FOREIGN PATENT DOCUMENTS

EP    2 090 326    8/2009
WO    2008/077706    7/2008

*Primary Examiner* — Bradley J Osinski
*Assistant Examiner* — Nilay Shah
(74) *Attorney, Agent, or Firm* — Thomas | Horstemeyer, LLP

(57) ABSTRACT

A needle tip assembly for a pre-loaded syringe or a pen needle injection device. The needle tip assembly includes a body comprising a double-ended needle and being installable and removable from the pre-loaded syringe or pen needle injection device. A needle cap is configured to cover a skin puncturing end of the double-ended needle and is removable to exposed the skin puncturing end. An outer cover is structured and arranged to at least install the body onto the pre-loaded syringe or pen needle injection device and remove the body from the pre-loaded syringe or pen needle injection device after the outer cover is re-installed. The body is lockable to the outer cover upon one of re-installation of the outer cover and prior to the body being removed from the pre-loaded syringe or pen needle injection device.

10 Claims, 21 Drawing Sheets

(52) U.S. Cl.
CPC ............ *A61M 5/34* (2013.01); *A61M 5/3205* (2013.01); *A61M 5/3213* (2013.01)

(56) References Cited

U.S. PATENT DOCUMENTS

| | | | |
|---|---|---|---|
| 4,973,318 A | 11/1990 | Holm et al. | |
| 5,242,401 A | 9/1993 | Colsky | |
| 5,242,416 A | 9/1993 | Hutson | |
| 5,389,085 A | 2/1995 | D'Alessio et al. | |
| 5,419,773 A | 5/1995 | Rupp | |
| 5,454,828 A | 10/1995 | Schraga | |
| 5,591,138 A | 1/1997 | Vaillancourt | |
| 5,593,387 A | 1/1997 | Rupp | |
| 5,611,786 A | 3/1997 | Kirchhofer et al. | |
| 5,879,345 A * | 3/1999 | Aneas .................. | A61J 1/2089 215/277 |
| 5,941,857 A * | 8/1999 | Nguyen .............. | A61M 5/3205 604/195 |
| 5,980,488 A | 11/1999 | Thorne | |
| 6,117,108 A | 9/2000 | Woehr et al. | |
| D445,602 S | 7/2001 | Tonon | |
| 6,287,278 B1 | 9/2001 | Woehr et al. | |
| 6,379,333 B1 | 4/2002 | Brimhall et al. | |
| 6,391,003 B1 | 5/2002 | Lesch, Jr. | |
| 6,460,234 B1 | 10/2002 | Gianchandani | |
| 6,470,754 B1 | 10/2002 | Gianchandani | |
| 6,616,630 B1 | 9/2003 | Woehr et al. | |
| 6,652,490 B2 | 11/2003 | Howell | |
| 6,749,588 B1 | 6/2004 | Howell et al. | |
| 6,855,129 B2 | 2/2005 | Jensen et al. | |
| 7,125,397 B2 | 10/2006 | Woehr et al. | |
| 7,160,269 B2 | 1/2007 | Woehr | |
| 7,214,211 B2 | 5/2007 | Woehr et al. | |
| 7,264,613 B2 | 9/2007 | Woehr et al. | |
| 7,462,168 B2 | 12/2008 | Stonehouse et al. | |
| 7,540,858 B2 | 6/2009 | DiBiasi | |
| 7,553,293 B2 | 6/2009 | Jensen et al. | |
| 7,871,397 B2 | 1/2011 | Schraga | |
| 2002/0004648 A1 | 1/2002 | Larsen et al. | |
| 2002/0133122 A1 | 9/2002 | Giambattista et al. | |
| 2003/0014018 A1 | 1/2003 | Giambattista et al. | |
| 2003/0105431 A1 | 6/2003 | Howell | |
| 2003/0195471 A1 | 10/2003 | Woehr et al. | |
| 2004/0116856 A1 | 6/2004 | Woehr et al. | |
| 2004/0186434 A1 | 9/2004 | Harding et al. | |
| 2004/0204681 A1 | 10/2004 | Thoresen et al. | |
| 2004/0220532 A1 | 11/2004 | Caizza | |
| 2004/0236284 A1 | 11/2004 | Hoste et al. | |
| 2004/0236288 A1 | 11/2004 | Howell | |
| 2005/0004532 A1 | 1/2005 | Woehr et al. | |
| 2005/0038392 A1 | 2/2005 | DeSalvo | |
| 2005/0080378 A1 | 4/2005 | Cindrich et al. | |
| 2005/0107748 A1 | 5/2005 | Thorne et al. | |
| 2005/0171485 A1 | 8/2005 | Larsen et al. | |
| 2005/0277881 A1 | 12/2005 | Sibbitt | |
| 2005/0277895 A1 | 12/2005 | Giambattista et al. | |
| 2005/0283115 A1 | 12/2005 | Giambattista et al. | |
| 2006/0229652 A1 | 10/2006 | Iio et al. | |
| 2006/0264828 A1 | 11/2006 | Woehr et al. | |
| 2007/0049868 A1 | 3/2007 | Woehr et al. | |
| 2007/0083159 A1 | 4/2007 | Woehr et al. | |
| 2007/0100297 A1 | 5/2007 | Woehr et al. | |
| 2007/0129689 A1 | 6/2007 | Woehr et al. | |
| 2007/0203458 A1 | 8/2007 | Tsubota | |
| 2007/0255225 A1 | 11/2007 | Alchas | |
| 2008/0108951 A1 | 5/2008 | Jerde et al. | |
| 2008/0154192 A1 * | 6/2008 | Schraga ................ | A61M 5/347 604/110 |
| 2008/0177237 A1 | 7/2008 | Stonehouse et al. | |
| 2008/0177238 A1 | 7/2008 | Follman et al. | |
| 2009/0069753 A1 | 3/2009 | Ruan et al. | |
| 2009/0254042 A1 | 10/2009 | Gratwohl et al. | |
| 2010/0114035 A1 | 5/2010 | Schubert | |
| 2010/0292654 A1 | 11/2010 | Schraga | |
| 2011/0022001 A1 | 1/2011 | Wei | |
| 2011/0077615 A1 | 3/2011 | Schraga | |
| 2011/0106016 A1 | 5/2011 | Wei | |
| 2011/0118667 A1 | 5/2011 | Zaiken et al. | |
| 2011/0160675 A1 | 6/2011 | Ruan et al. | |
| 2011/0288526 A1 | 11/2011 | Wei | |

\* cited by examiner

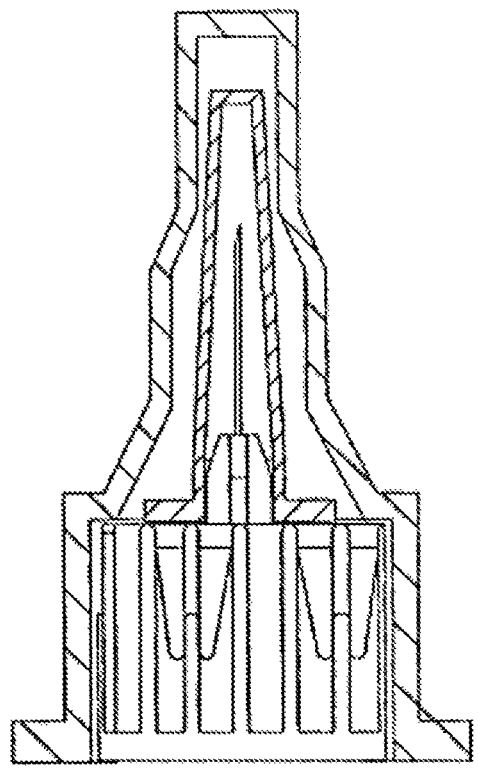
FIG. 2
PRIOR ART
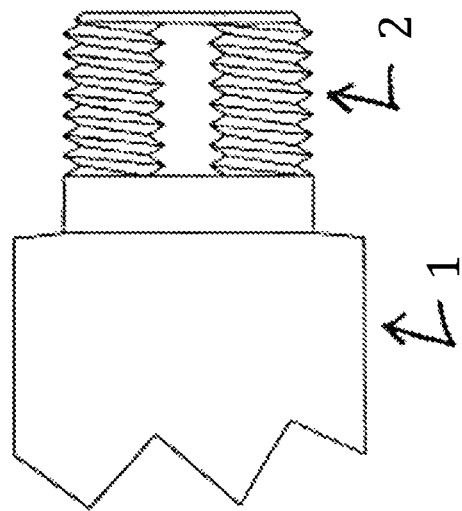

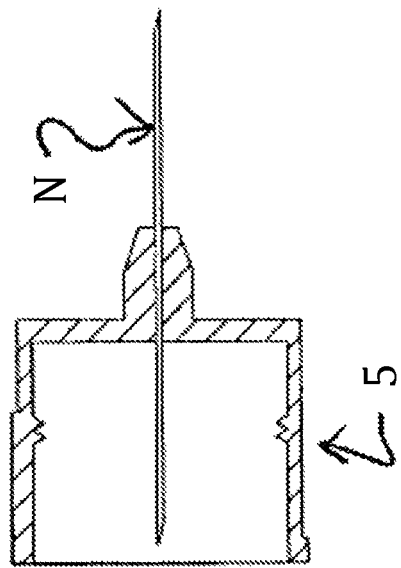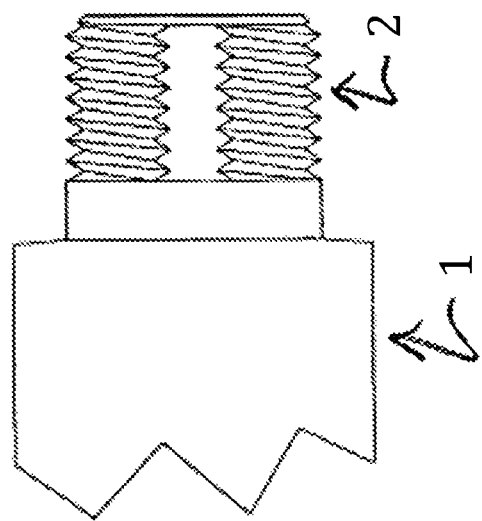
FIG. 6
PRIOR ART

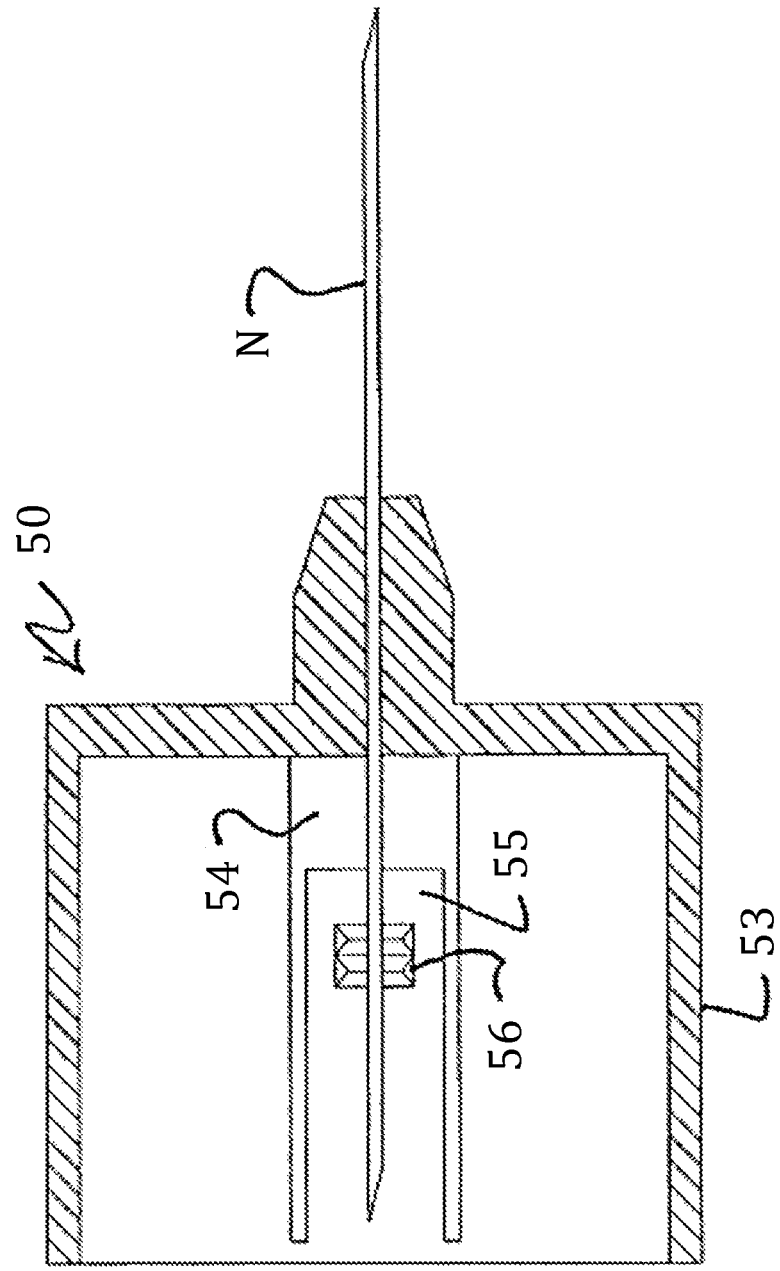

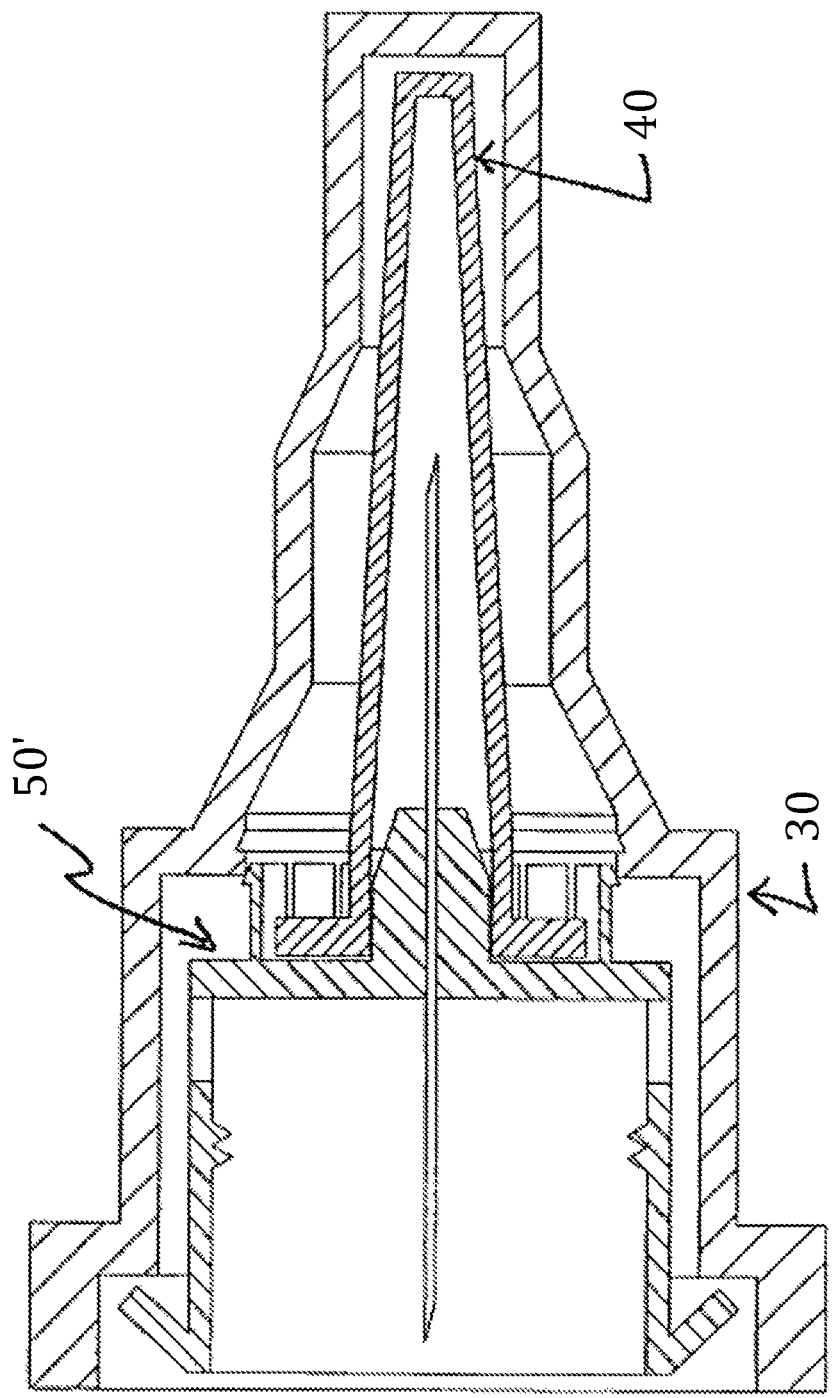

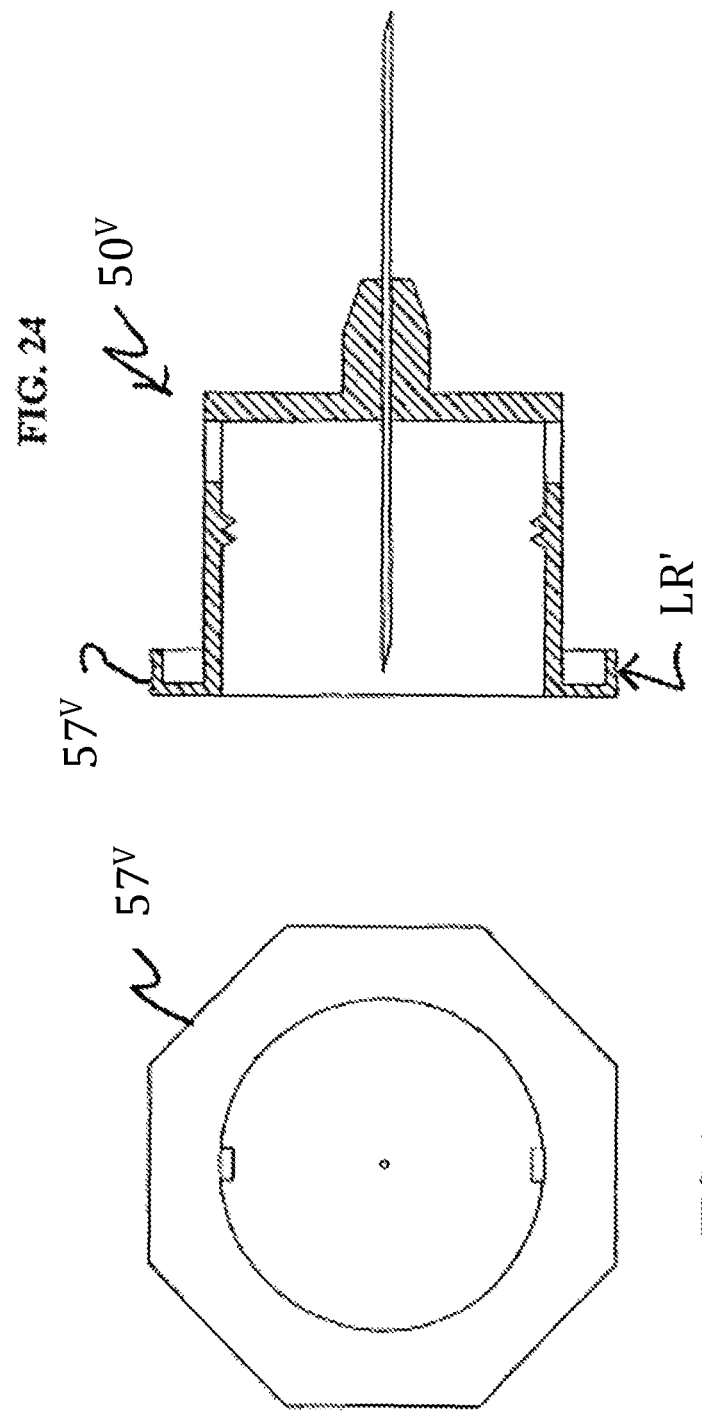

PEN NEEDLE INSTALLATION AND REMOVAL SAFETY COVER AND PEN NEEDLE ASSEMBLY UTILIZING THE SAME

CROSS-REFERENCE TO RELATED APPLICATIONS

The instant application is a US non-provisional application that is based on and claims the benefit of U.S. provisional application No. 61/982,030, filed Apr. 21, 2014, the disclosure of which is hereby expressly incorporated by reference thereto in its entirety.

BACKGROUND OF THE INVENTION

1. Field of the Invention

This invention relates generally to pen needles, e.g., pre-loaded syringes, such are utilized for injection of medicament into the body tissues of human and animal patients. More specifically, this invention relates to a pen needle or pen needle tip or pen needle tip system which can be prevented from reuse.

2. Discussion of Background Information

U.S. Pat. No. 7,871,397, the disclosure of which is hereby expressly incorporated by reference in its entirety, discloses various embodiments of a pen needle tip and teaches one or more embodiments that utilizes a mechanism for preventing reuse of the pen needle.

FIGS. 1-6 of the instant application show a prior art pen needle assembly of the type mentioned in U.S. Pat. No. 7,871,397. This assembly includes a pull-tab sealing member PT removably and sealing secured to a packaging outer body 3. Once removed, the user can install the same on the threaded or pen needle receiving end 2 of a pre-loaded syringe 1 as shown in FIGS. 2 and 3. The user then removes the outer body 3 to reveal and uncover the installed pen needle 5. In order to perform an injection, the user then removes the needle cover 4—which exposes the injection portion of needle N. After injection, the user can remove the pen needle 5 as shown in FIG. 6.

Although the invention disclosed in U.S. Pat. No. 7,871,397 is believed to be a significant improvement over the prior art, it is desirable to provide a pen needle system which is even safer and/or easier to use compared to the conventional devices discussed above and/or which does not have one or more of the above-noted disadvantageous.

SUMMARY OF THE INVENTION

According to one non-limiting embodiment of the invention, there is provided a pen needle or pen needle tip assembly having a removable tip which can be prevented from reuse and/or which utilizes one or more mechanisms for preventing the possibility of inadvertent needle pricks.

According to another non-limiting embodiment of the invention, there is provided a pen needle tip for a pen needle wherein the pen needle tip assembly is configured to prevent it from being re-used.

According to another non-limiting embodiment of the invention, there is provided a needle tip for a device such as, e.g., a pre-loaded syringe, which can be used only once, i.e., single-use tips, and/or to tips which include one or more mechanisms for preventing the user from being pricked when handling the tip.

According to another non-limiting embodiment of the invention there is provided a needle tip assembly for a pre-loaded syringe or a pen needle injection device. The needle tip assembly includes a body comprising a double-ended needle and being installable and removable from the pre-loaded syringe or pen needle injection device. A needle cap is configured to cover a skin puncturing end of the double-ended needle and is removable to exposed the skin puncturing end. An outer cover is structured and arranged to at least install the body onto the pre-loaded syringe or pen needle injection device and remove the body from the pre-loaded syringe or pen needle injection device after the outer cover is re-installed. The body is lockable to the outer cover upon one of re-installation of the outer cover and prior to the body being removed from the pre-loaded syringe or pen needle injection device.

According to another non-limiting embodiment of the invention, the outer cover is structured and arranged to contain therein the body and the needle cap in a prior use and packaged condition.

According to another non-limiting embodiment of the invention, the body is a one-piece body.

According to another non-limiting embodiment of the invention, the outer cover is a one-piece body.

According to another non-limiting embodiment of the invention, the needle cap is a one-piece body.

According to another non-limiting embodiment of the invention, the outer cover has an axial length that is greater than an axial length of the body.

According to another non-limiting embodiment of the invention, the outer cover has an axial length that is greater than an axial length of the needle cap.

According to another non-limiting embodiment of the invention, there is provided a needle tip assembly for a pre-loaded syringe or a pen needle injection device, the needle tip assembly comprising a body comprising a double-ended needle and being installable and removable from the pre-loaded syringe or pen needle injection device, an outer cover structured and arranged to at least contain therein the body and the needle cap in a prior use and packaged condition, install the body onto the pre-loaded syringe or pen needle injection device, and remove the body from the pre-loaded syringe or pen needle injection device after the outer cover is re-installed. The body is lockable to the outer cover upon one of re-installation of the outer cover and prior to the body being removed from the pre-loaded syringe or pen needle injection device.

According to another non-limiting embodiment of the invention, there is provided a needle tip assembly for a pre-loaded syringe or a pen needle injection device, wherein the needle tip assembly comprises a body comprising a double-ended needle and being installable and removable from the pre-loaded syringe or pen needle injection device, an outer cover structured and arranged to at least contain therein the body and the needle cap in a prior use and packaged condition, install the body onto the pre-loaded syringe or pen needle injection device, and remove the body from the pre-loaded syringe or pen needle injection device without requiring rotation thereof after the outer cover is re-installed. The body is lockable to the outer cover upon one of re-installation of the outer cover and prior to the body being removed from the pre-loaded syringe or pen needle injection device.

According to another non-limiting embodiment of the invention, there is provided a needle tip assembly for a pre-loaded syringe or a pen needle injection device, the needle tip assembly comprising a body comprising a double-ended needle and being installable and removable from the pre-loaded syringe or pen needle injection device, an outer cover structured and arranged to at least install the body onto the pre-loaded syringe or pen needle injection device utilizing a rotation movement thereof and remove the body from the pre-loaded syringe or pen needle injection device without requiring rotation thereof after the outer cover is re-installed. The body is lockable to the outer cover upon one of re-installation of the outer cover and prior to the body being removed from the pre-loaded syringe or pen needle injection device.

According to another non-limiting embodiment of the invention, there is provided a method of installing the assembly of anyone of types described herein on a pre-loaded syringe or a pen needle injection device, wherein the method comprises prior to use during injection, installing as a unit the outer cover, the needle cap and the body with the double-ended needle, removing the needle cap prior to injection, after injection, moving the outer cover to a locked position, and after the moving, removing the outer cover with the body disposed therein from the pre-loaded syringe or pen needle injection device.

According to another non-limiting embodiment of the invention, there is provided a method of making the assembly of anyone of the types described herein, wherein the method comprises installing within the outer cover, the needle cap and the body with the double-ended needle in a manner which prevents a locking engagement between the body and the outer cover.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 2 shows the prior art needle tip assembly as it is about to be installed onto a proximal end of a prior art pen needle or pre-loaded syringe/injection device;

FIG. 6 shows the needle tip being removed from the pen needle device according to the prior art. This would occur after use and can occur by unthreading the needle tip from the threaded proximal end of the pen needle device. As is apparent, it is possible to re-install the needle tip onto the threaded proximal end of the pen needle device;

FIG. 9 shows a side cross-section view of the needle tip or pen needle of FIG. 7 rotated 90 degrees;

FIG. 10 shows a needle tip assembly according to one embodiment of the invention and utilizing the needle tip shown in FIG. 7. An optional pull-tab type sealing member of the type shown in FIG. 1 has been removed. As should be apparent, the needle cover prevents the outer cover from being locked to the needle tip or body;

FIGS. 24 and 25 show end and side cross-section views of another embodiment of a needle tip or body and that can be utilized with the outer cap shown in FIGS. 22 and 23.

DETAILED DESCRIPTION OF THE INVENTION

The present invention is further described in the detailed description which follows, in reference to exemplary embodiments.

Figure 8:
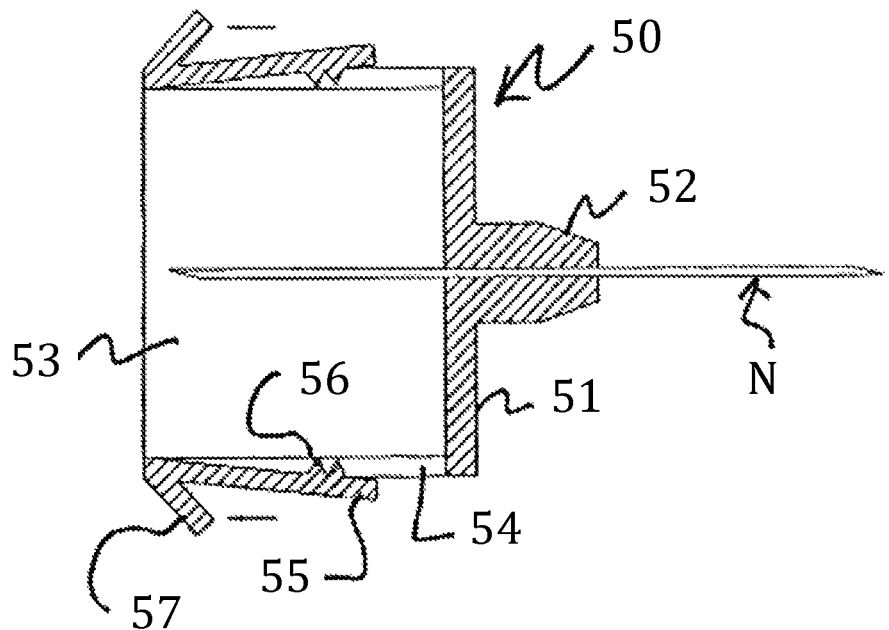
FIG. 8 shows a side cross-section view of the needle tip or pen needle of FIG. 7 but after its engaging thread section are moved to a disengaged position.
Figure 7:
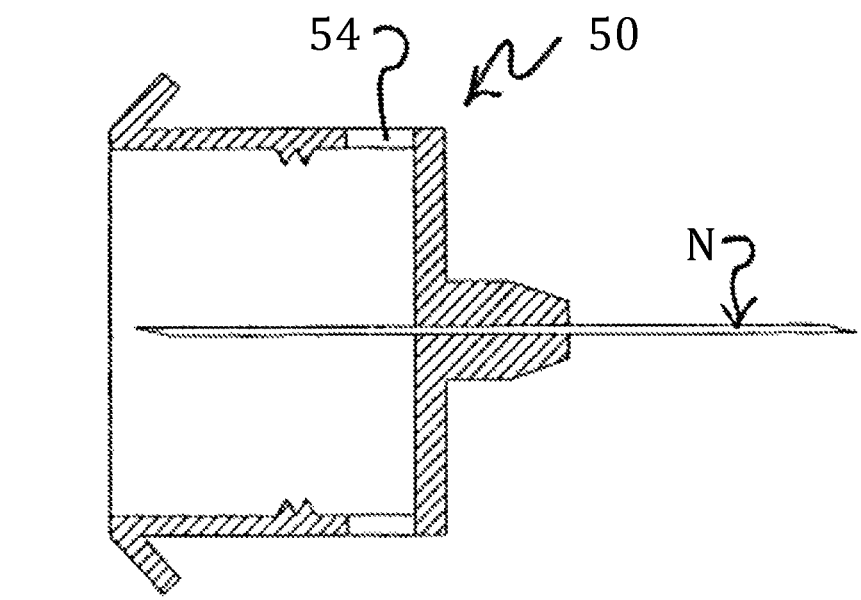
FIG. 7 shows a side cross-section view of an exemplary needle tip or pen needle according to the invention.

In the non-limiting embodiment shown in FIGS. 7-9, there is shown a pen needle 50 which includes a main body 53 which can be generally cylindrical, a front or proximal annular wall 51, a hub 52, as well as a hollow double ended needle N. The needle N is axially secured or retained in the hub 52 and includes a front/proximal puncturing portion (having skin injection end) as well as a distal or rear puncturing portion (having an injection device puncturing end) that extends within the body 53. In order to help retain the pen needle 50 on an injection device 1 of the type shown in FIG. 2, the embodiment shown in FIGS. 7-9 utilizes thread engaging teeth or tooth segments 56 which project or protrude inwardly and are configured to engage (e.g., frictionally engaged) with the external thread of section 2 of the device 1 shown in FIG. 2. In order to facilitate installation and/or removal of the pen needle 50 from the section 2, the teeth 56 can be arranged on one or more deflectable portions or members 55. The one or more elements 55 are each arranged in a respective opening 54 formed in the body sidewall 53 and can be deflected outwardly under different conditions—as will be discussed below. In the embodiment shown in FIGS. 7-9, each element 55 is integrally formed with the sidewall 53, functions as a spring in that its relaxed position is that of FIG. 7 (as opposed to its deflected or biased position shown in FIG. 8) and a free or movable end of the element 55 is arranged in an area of the teeth 56 while a fixed end is located in an area of the distal end of the body sidewall 53 (see FIG. 9).

The conditions by which the non-limiting embodiment shown in FIGS. 7-9 may be installed or removed will now be discussed. Under one installation condition, a user merely slides the pen needle 50 onto the section 2 (preferably with a non-illustrated packaging body installed). This axial installation movement need not be accompanied by rotation of the pen needle 50 if the user so chooses. When the teeth 56 contact the threads of the section 2, they can deflect outwardly and inwardly owing to movement of the element 55 and this will continue until the pen needle 50 is fully installed. This movement can possibly create a ratchet-type sound as the teeth 56 movably engage with the thread of the section 2. Removal of the pen needle 50 can occur in an opposite matter with the user pulling the pen needle 50 off of the section 2. Alternatively, the user can simply rotate and unthread the pen needle 50 from the section 2.

Another condition by which the non-limiting embodiment shown in FIGS. 7-9 may be installed or removed will now be discussed. Under an alternative installation condition, a user merely slides the pen needle 50 onto the section 2 with a packing body (similar to packaging body 30 shown in FIG. 10) installed and this axial installation movement is not accompanied by rotation of the pen needle 50. Instead, the packing body (not shown) exerts a force in the direction of arrows shown in FIG. 8 during the sliding on. This force is exerted against the portion 57 which causes its movement and this movement in turn causes the element 55 to deflect outwardly. In this way, the pen needle 50 is fully installed without the teeth 56 engaging with the thread of the section 2 until full installation is reached. Removal of the pen needle 50 can occur in an opposite matter with the user sliding on the packing body until the pen needle 50 assumes the position shown in FIG. 8, and then pulling the pen needle 50 off of the section 2. Alternatively, the user can simply pull it off as in the above-noted condition or unthread the pen needle 50 from the section 2.

In order to make the non-limiting embodiment shown in FIGS. 7-9 with lower cost, the pen needle body can be a one-piece integrally formed synthetic resin member with elements 51-57. The needle N can be made of metal as is the case with typical pen needles. In the embodiment shown in FIGS. 7-9, two oppositely arranged deflectable elements 55 (each with teeth 56 and projection 57) are used. However, the invention contemplates using only one as well as any number of the same such 3, 4, 5, 6, 7, 8, etc. With two or more, they be equally circumferentially spaced around the sidewall 53.

Figure 1:
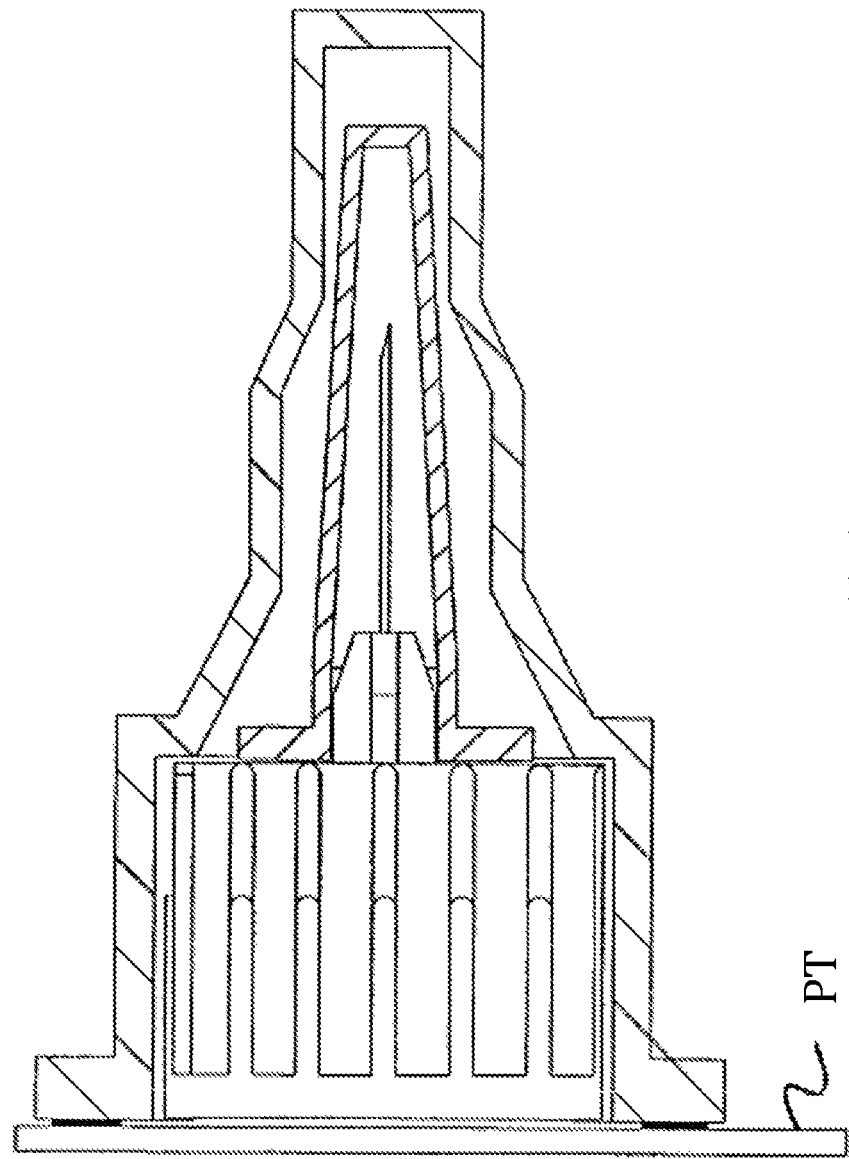
FIG. 1 shows an enlarged side view of a prior art packaged needle tip assembly.
Figure 3:
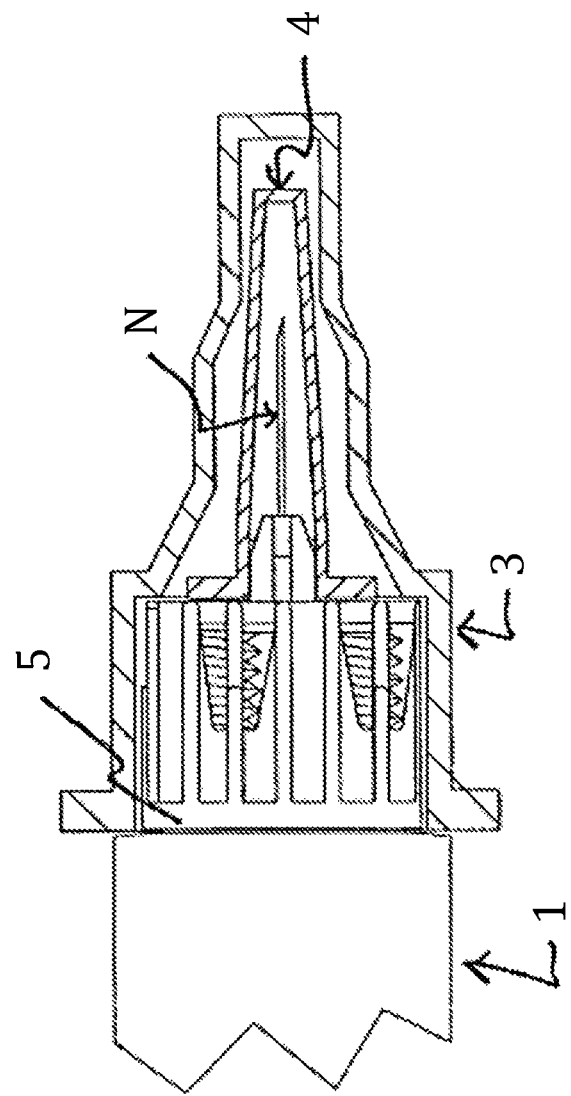
FIG. 3 shows the needle tip assembly of FIG. 2 in an installed condition.
Figure 4:
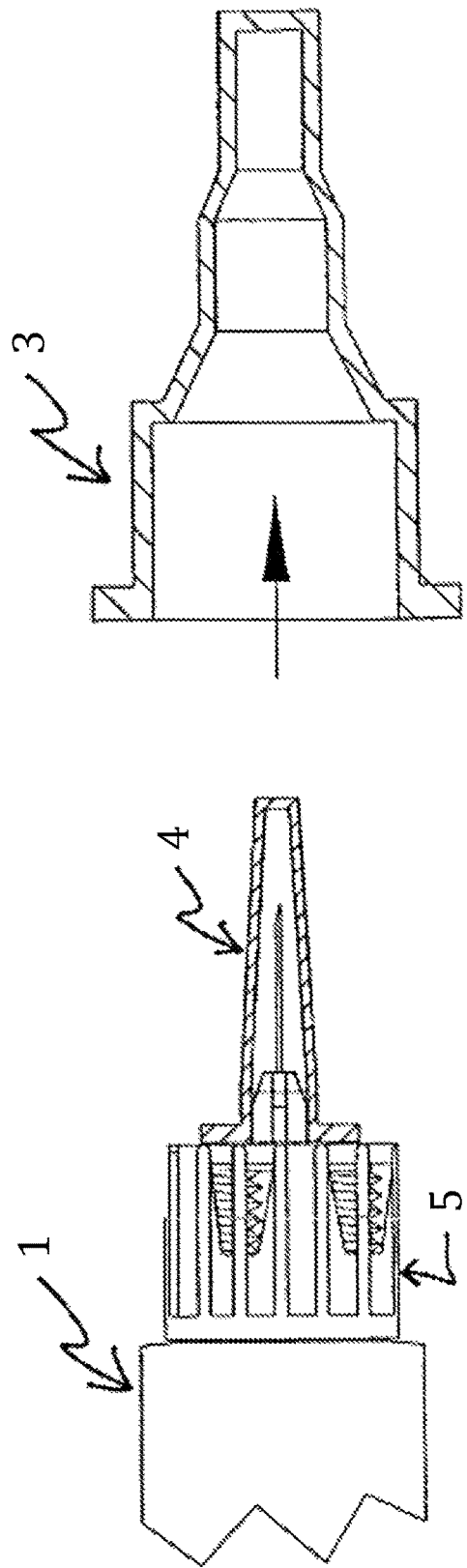
FIG. 4 shows the configuration of FIG. 3 after the outer cover is removed.
Figure 5:
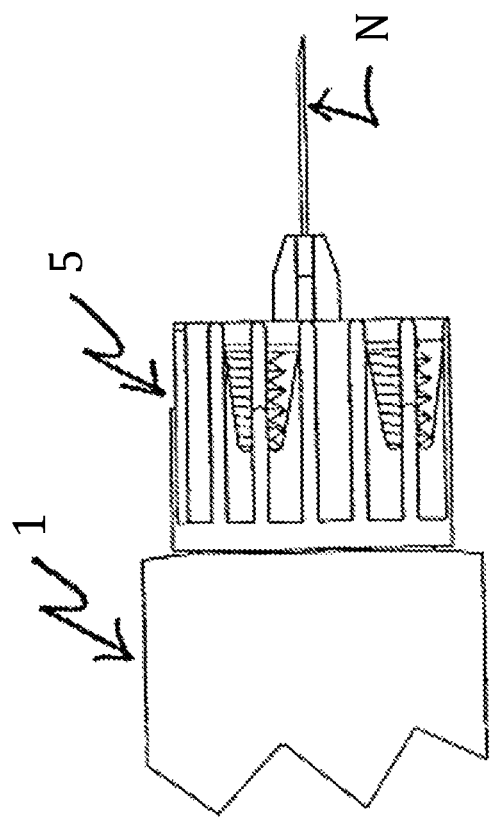
FIG. 5 shows the configuration of FIG. 4 after the needle cover is removed whereby the needle tip mounted onto the pen needle device in a position ready for injection according to the prior art.
Figure 11:
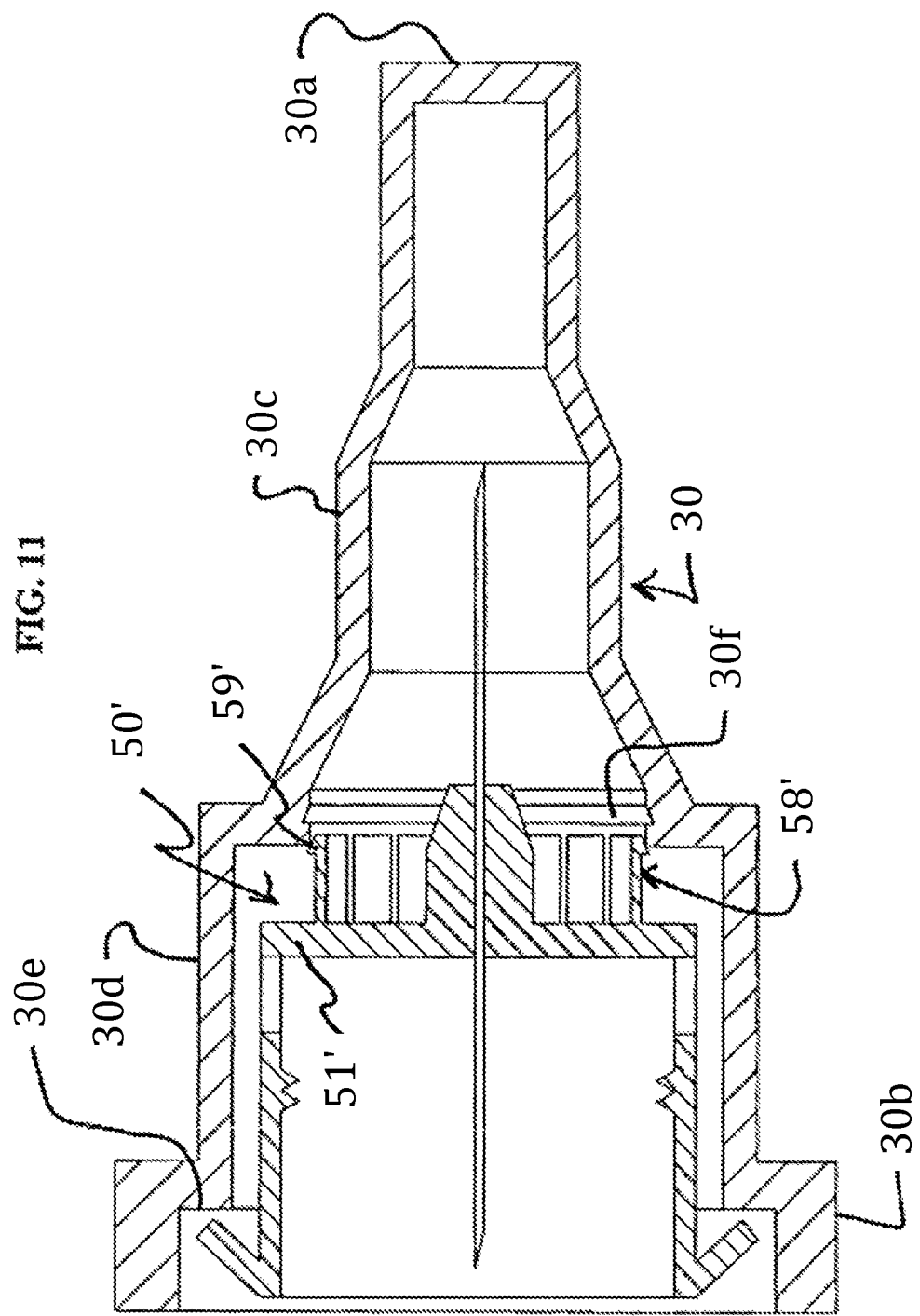
FIG. 11 shows a needle tip assembly of FIG. 10 with the needle cover removed and illustrates that, in this condition, nothing prevents the outer cover from being locked to the needle tip or body. This condition would typically occur when the outer cover is partially re-installed and after injection. For clarity, the pre-loaded syringe is not shown.
Figure 12:
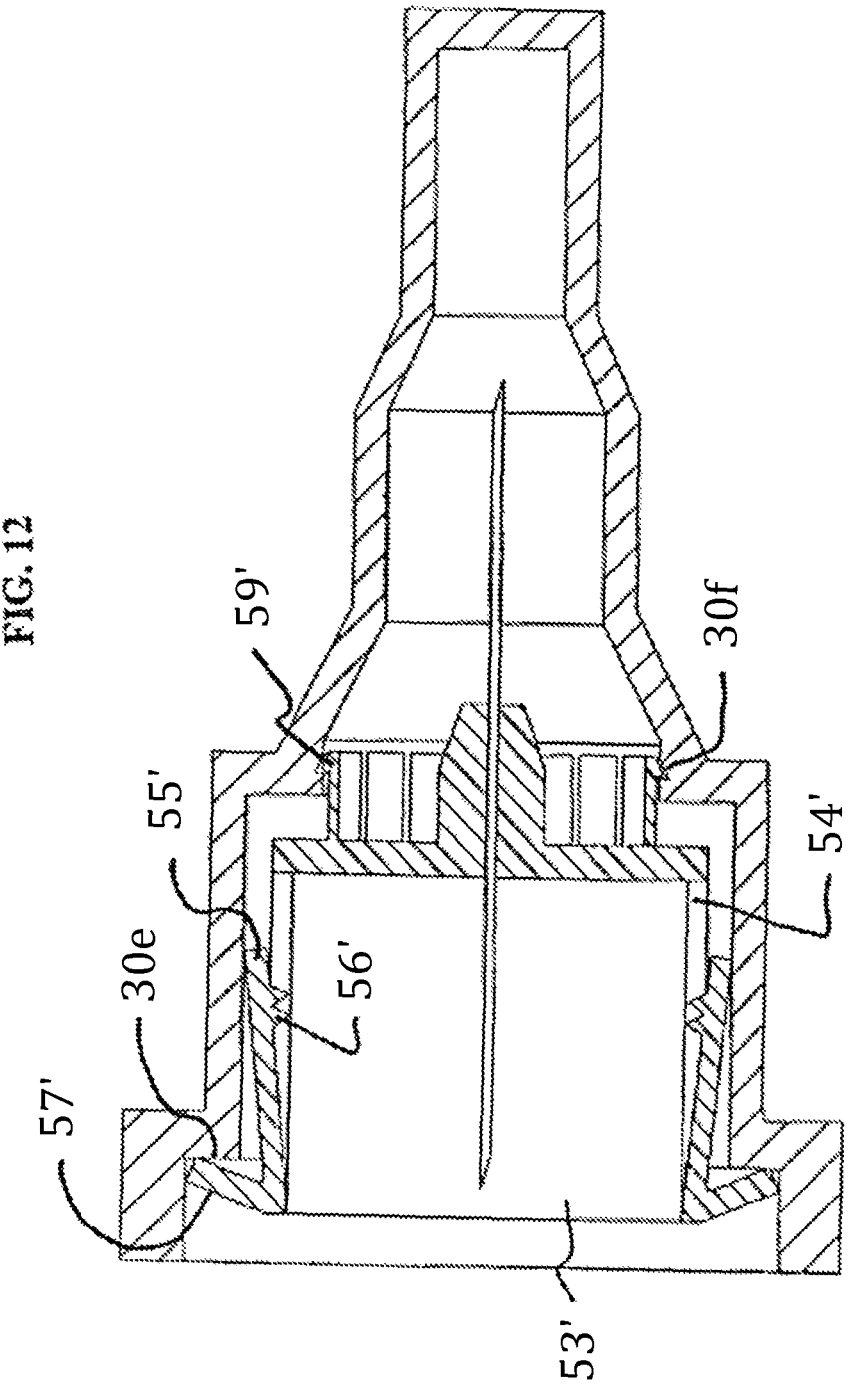
FIG. 12 shows a needle tip assembly of FIG. 11 with the outer cover non-releasably or permanently locked to the needle tip or body. This condition would typically occur when the outer cover is fully re-installed and after injection. For clarity, the pre-loaded syringe is not shown. In this condition, the thread sections of the body or needle tip are in a disengaged position.

FIGS. 10-14 show a non-limiting embodiment of a pen needle assembly which utilizes a pen needle 50' that is similar to the previous embodiment. Although not shown in FIGS. 10-14, this embodiment (as well as others described herein) can utilize a packaging seal member having a pull-tab similar to that shown in FIG. 1. As in the prior art, the purpose of such a seal is, among other things, to preserve the sterile state of the pen needle and prevent pre-use contamination. An exemplary condition by which the non-limiting embodiment shown in FIGS. 10-14 may be installed or removed will now be discussed. Under an installation condition, a user merely slides the pen needle 50' onto the section 2 by gripping the packing body 30 while the needle cap 40 is installed on the hub (as shown in FIG. 10). During installation, an annular surface 30*e* of the packing body 30 exerts a force on element(s) 57'. This force is exerted against the portion 57' which causes its movement and this movement in turn causes the element 55' to deflect outwardly. In this way, the pen needle 50' is fully installed without the teeth 56' engaging (or only lightly engaging) with the thread of the section 2—until full installation is reached. With the needle cap 40 installed as shown in FIG. 10, the pen needle 50' cannot become (or is prevented from being) locked to the packaging body 30. This is because the needle cap 40 has an axial length that is of sufficient length to prevent such locking movement and because the distance between the front end of the cap 40 and the front wall 30*a* of the cover 30 is less than the separation distance between the locking projection 59' and locking recess 30*f*. After an injection and while the pen needle 50' remains installed on the section 2 (not shown in FIG. 11), a user can remove the pen needle 50' by installing the packing body 30 (without the needle cap 40) as shown in FIG. 11. Then, as shown in FIG. 12, the user slides on the packing body 30 fully over the installed pen needle 51' until the pen needle 50' assumes the non-releasably locked position shown in FIG. 12. Locking occurs when the projection 59' engages with the recess 30*f*. At this point, the user can pull the pen needle 50' off of the section 2 and discard the same. As should be apparent from FIG. 12, when the pen needle 50' becomes locked to the packaging body 30, the surface 30*e* continues to exert a force on the element(s) 57'—which causes the element 55' to deflect outwardly—whereby the teeth 56' are moved away from engagement with the thread of the section 2. With the pen needle 50' in the non-releasably locked position shown in FIG. 12, it can be more easily slid off as there is no longer engagement with the thread of the section 2. Rotation is not required for removal either. Essentially only the frictional engagement between the needle and the puncturable septum of the injection device 1 prevents removal of the pen needle 50'. Moreover, when the pen needle 50' is removed, it is safely positioned inside the cover or packaging body 30 which has functioned, in addition to packaging, as a removal tool, a re-use prevention device, and a safety shield. Disposal of the assembly shown in FIG. 12 can now more safely occur, i.e., during handling, the user and others are prevented by the cover 30 from being punctured by the needle N.

Figure 13:
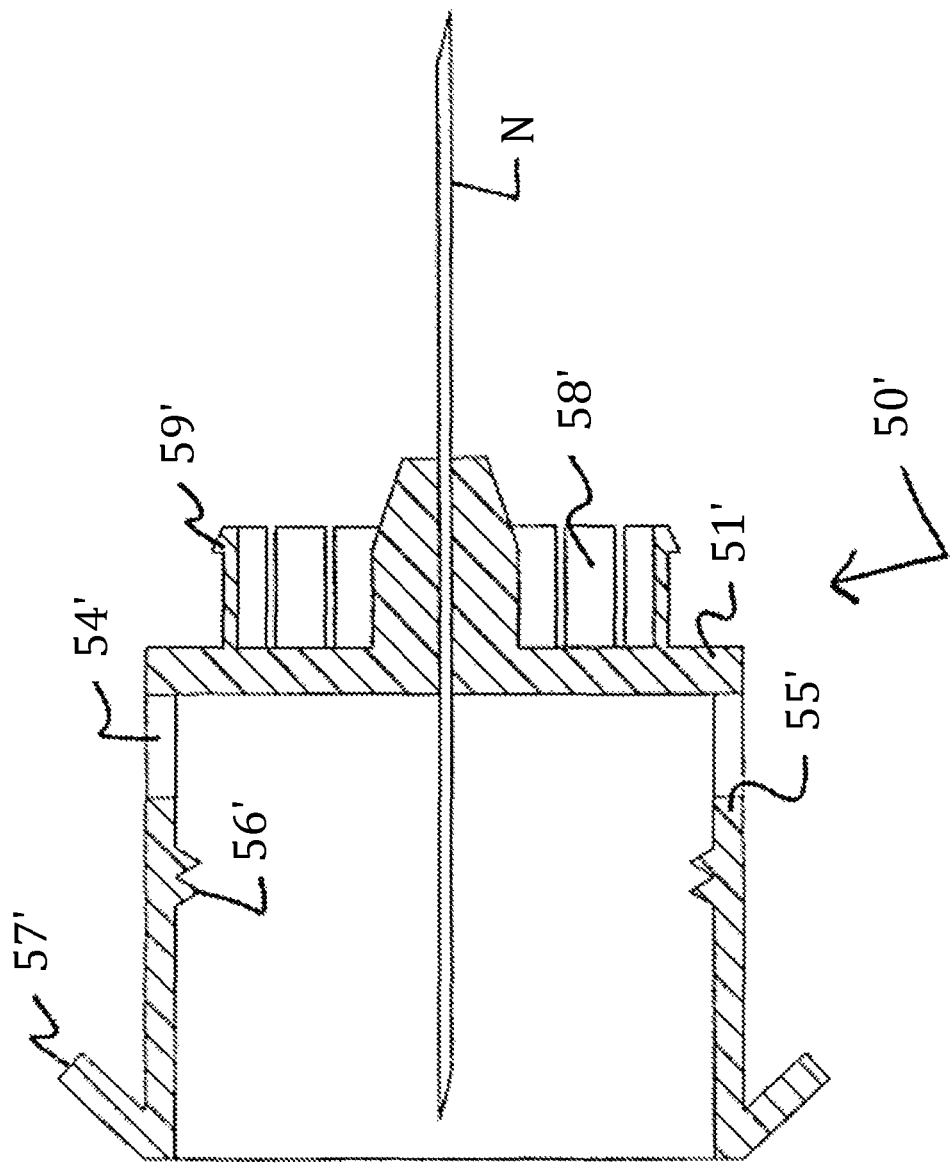
FIG. 13 shows the needle tip or body utilized in the embodiment shown in FIG. 10.
Figure 14:
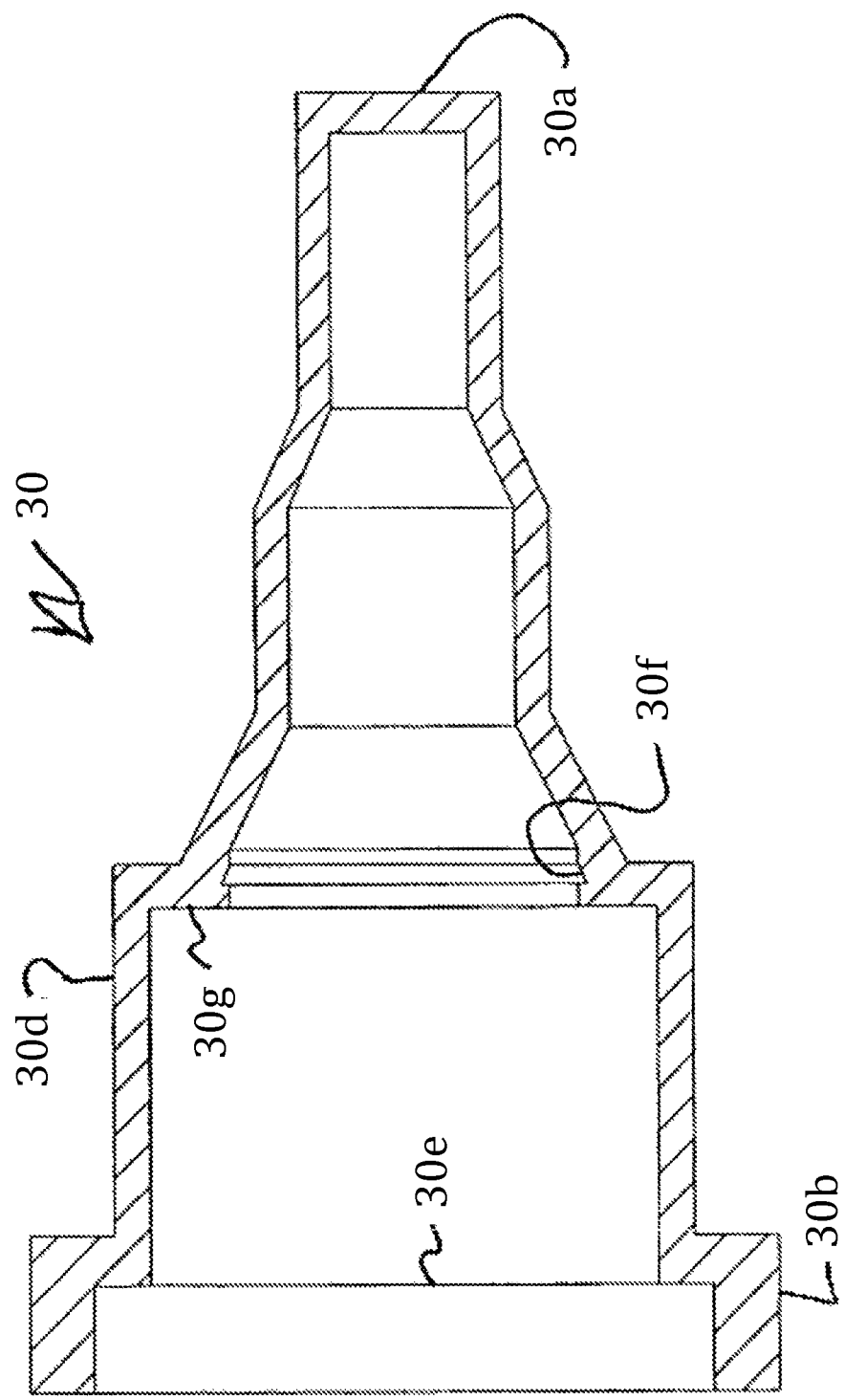
FIG. 14 shows the outer cover utilized in the embodiment shown in FIG. 10.

As can be seen in FIGS. 12-14, the pen needle 50' that is similar to the previous embodiment except that it additionally includes a locking collar 58' projecting from the wall 51'. The collar 58' can be segmented to allow for deflection and includes locking projection(s) 59' sized and configured to non-releasably engage with a recess 30f of the cover 30. The pen needle 50' includes a sidewall 53' with one or more openings 54' accommodating therein a deflectable element 55'. Each element 55' has one or more teeth 56' and is coupled to a activating portion 57'. To allow for outward deflection of the element(s) 55', the sidewall portion 30d of the cover 30 is made larger. The cover 30 also includes the above-discussed locking projection 30f, as well as an annular wall 30g, an installed section 30c, a proximal end 30a and distal end 30b.

In order to make the non-limiting embodiment shown in FIGS. 10-14 with lower cost, the pen needle body can be a one-piece integrally formed synthetic resin member with elements 51'-59'. The needle N can be made of metal as is the case with typical pen needles. In addition, the cap 30 can be a one-piece integrally formed synthetic resin member. Moreover, the invention contemplates that the collar 58' that is generally cylindrical and continuous rather than segmented as shown in FIG. 13.

Figure 15:
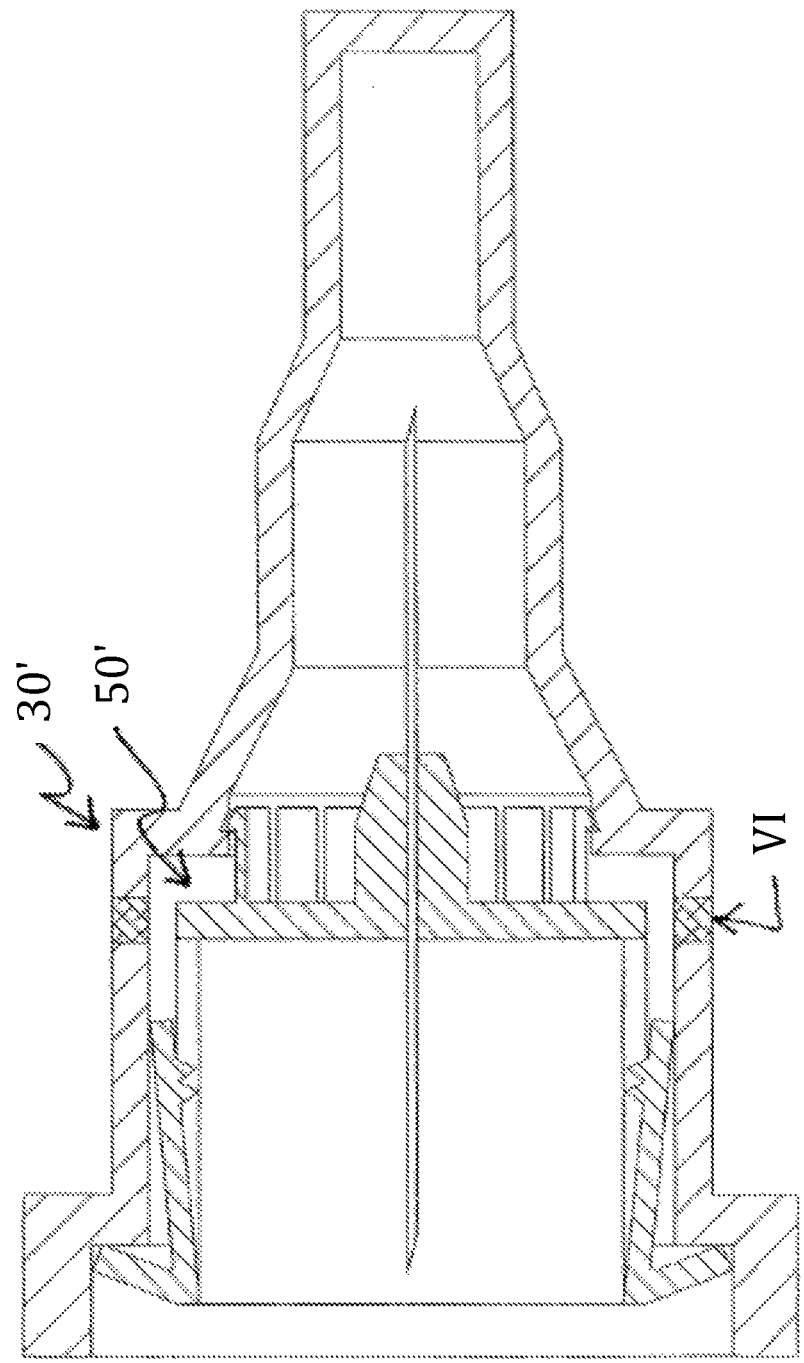
FIG. 15 shows a needle tip assembly according to still another embodiment of the invention, but in the locked condition to illustrate how one or more visual indicator windows can be provided in the outer cover in order to provide a visual indicator to the user that the assembly has been used, should not be used again, and can be safely discarded.

FIG. 15 shows a needle tip assembly according to still another embodiment of the invention, but in the locked post-use and removed condition. This embodiment is similar to that shown in FIG. 12 except that the cover 30' utilizes one or more window or visibility allowing sections VI. The one or more visual indicator windows VI can be provided in the outer cover 30' in order to provide a visual indicator to the user that the pen needle 50' disposed therein has been used and should not be used again. Thus, the person handling the assembly is provided with an indication that the assembly should be safely discarded. If for example, the pen needle sidewall is red in color and the cover 30' is opaque, the openings or windows VI will allow the user to see the red color when the pen needle 50' is in the locked position inside the cover 30'.

Figure 16:
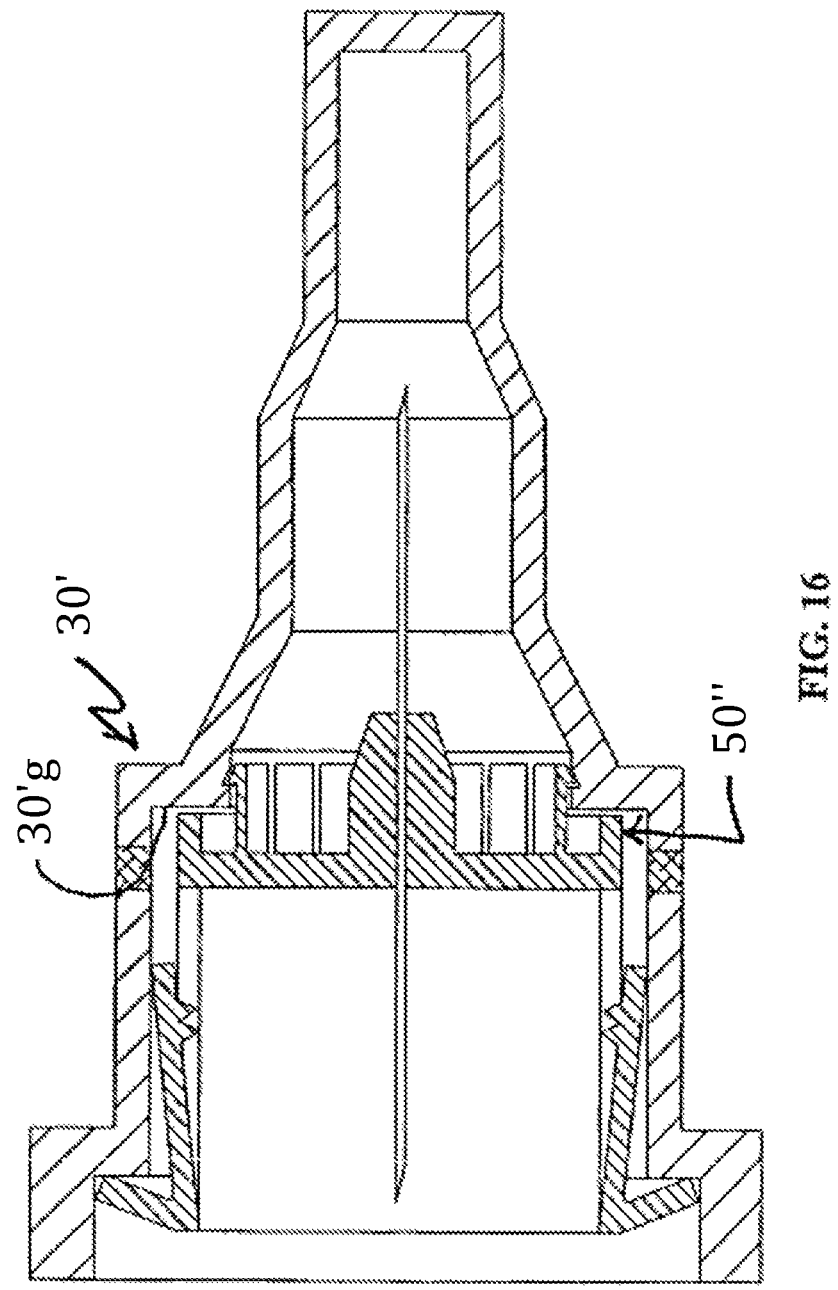
FIG. 16 shows a needle tip assembly according to still another embodiment of the invention, but in the locked condition to illustrate how one or more visual indicator windows can be provided in the outer cover in order to provide a visual indicator to the user that the assembly has been used, should not be used again, and can be safely discarded.

FIG. 16 shows a needle tip assembly according to still another embodiment of the invention. This embodiment is similar to that of FIG. 15 except that the pen needle 50" is modified so as to include an integrally formed cylindrical projecting flange whose proximal end is configured to abut the annular surface 30'g of the cover 30' when the pen needle 50" becomes locked to the cover 30'.

Figure 17:
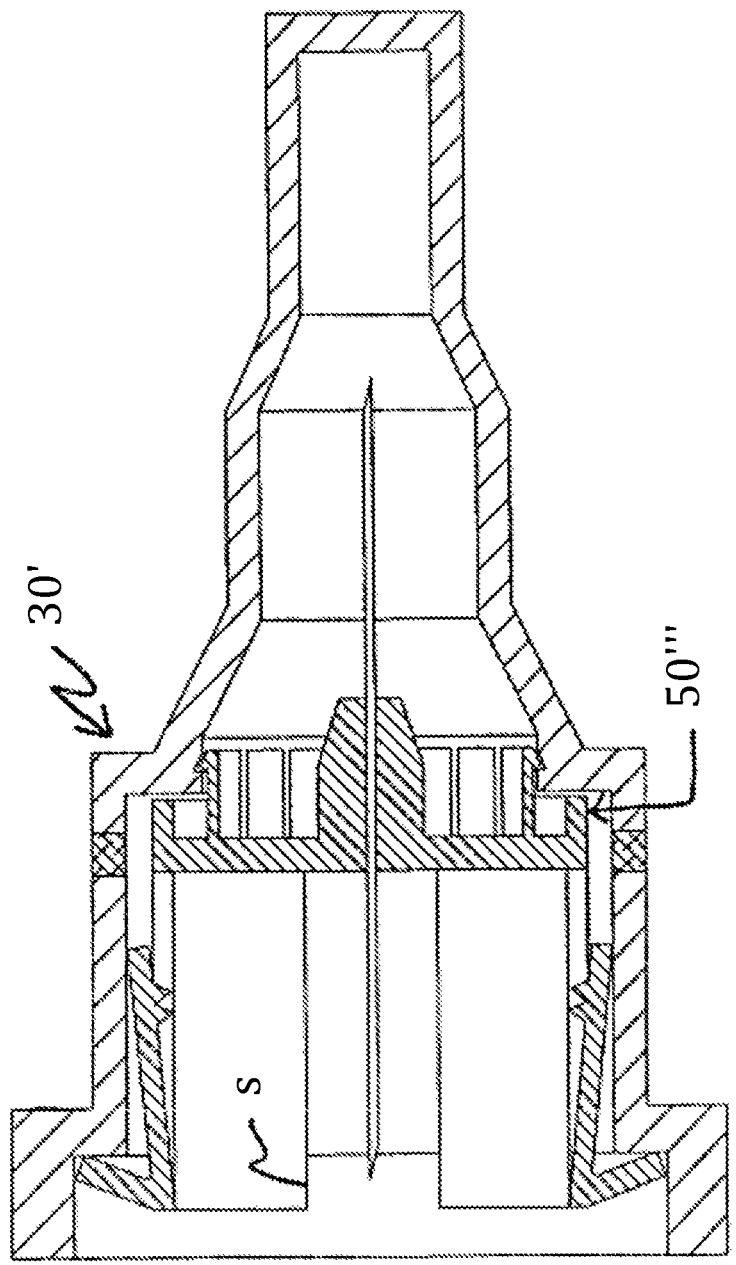
FIG. 17 shows a needle tip assembly according to still another embodiment of the invention, but in the locked condition to illustrate how one or more visual indicator windows can be provided in the outer cover in order to provide a visual indicator to the user that the assembly has been used, should not be used again, and can be safely discarded. In this embodiment, the body utilizes one or more sidewall slots.

FIG. 17 shows a needle tip assembly according to still another embodiment of the invention. This embodiment is similar to that of FIG. 16 except that the pen needle 50''' is modified so as to include one or more sidewall through slot(s) S formed on the cylindrical sidewall of the pen needle 50". Each slot(s) S can extend from a distal end to the wall having the hub as shown in FIG. 17 and allows for, among other things, a user to visually see the thread of the section 2 to determine whether a proper fully installed condition is reached.

Figure 18:
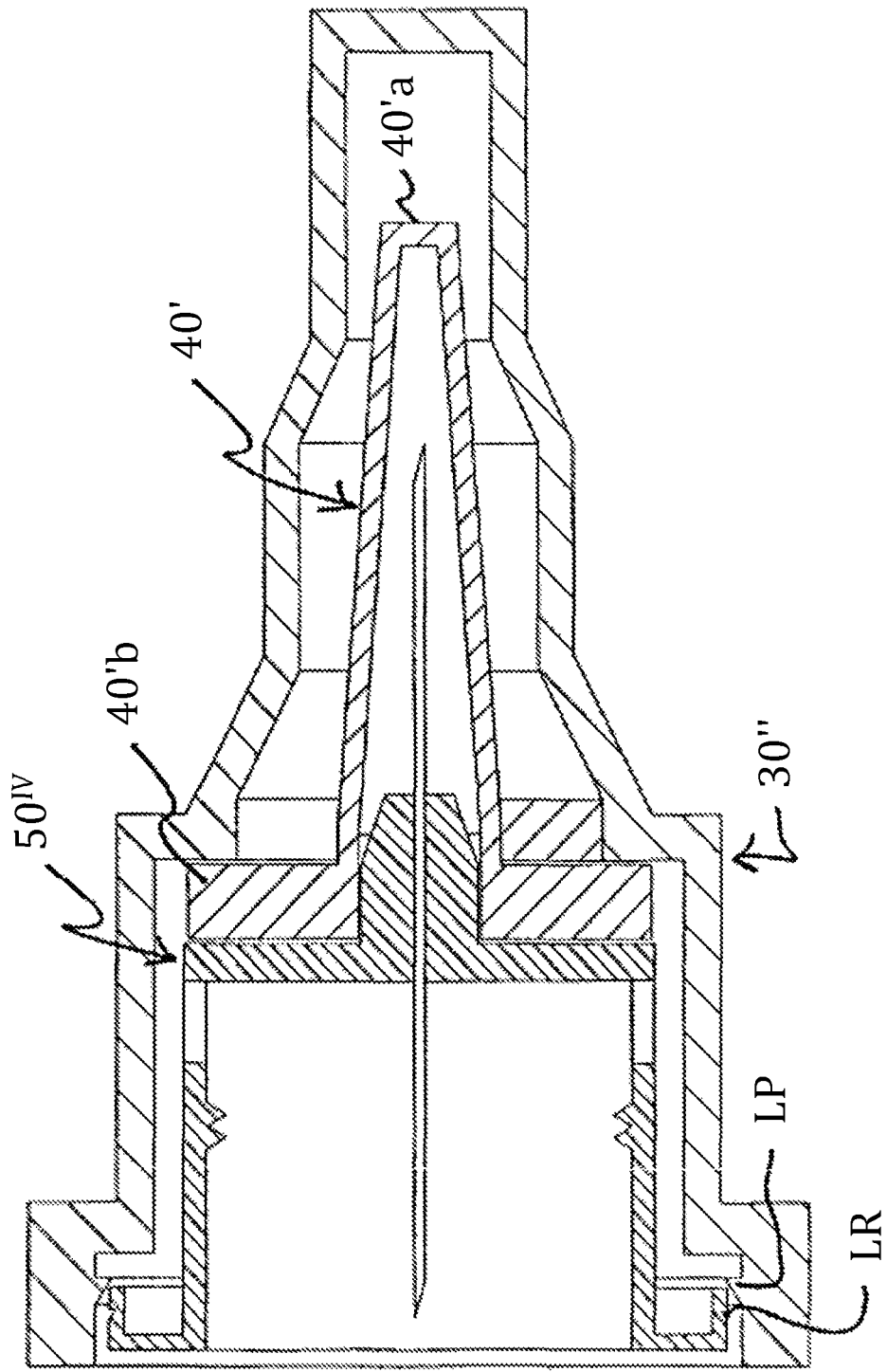
FIG. 18 shows a needle tip assembly according to one embodiment of the invention. An optional pull-tab type sealing member of the type shown in FIG. 1 has been removed. As should be apparent, a flange portion of the needle cover prevents the outer cover from being locked to the needle tip or body.
Figure 19:
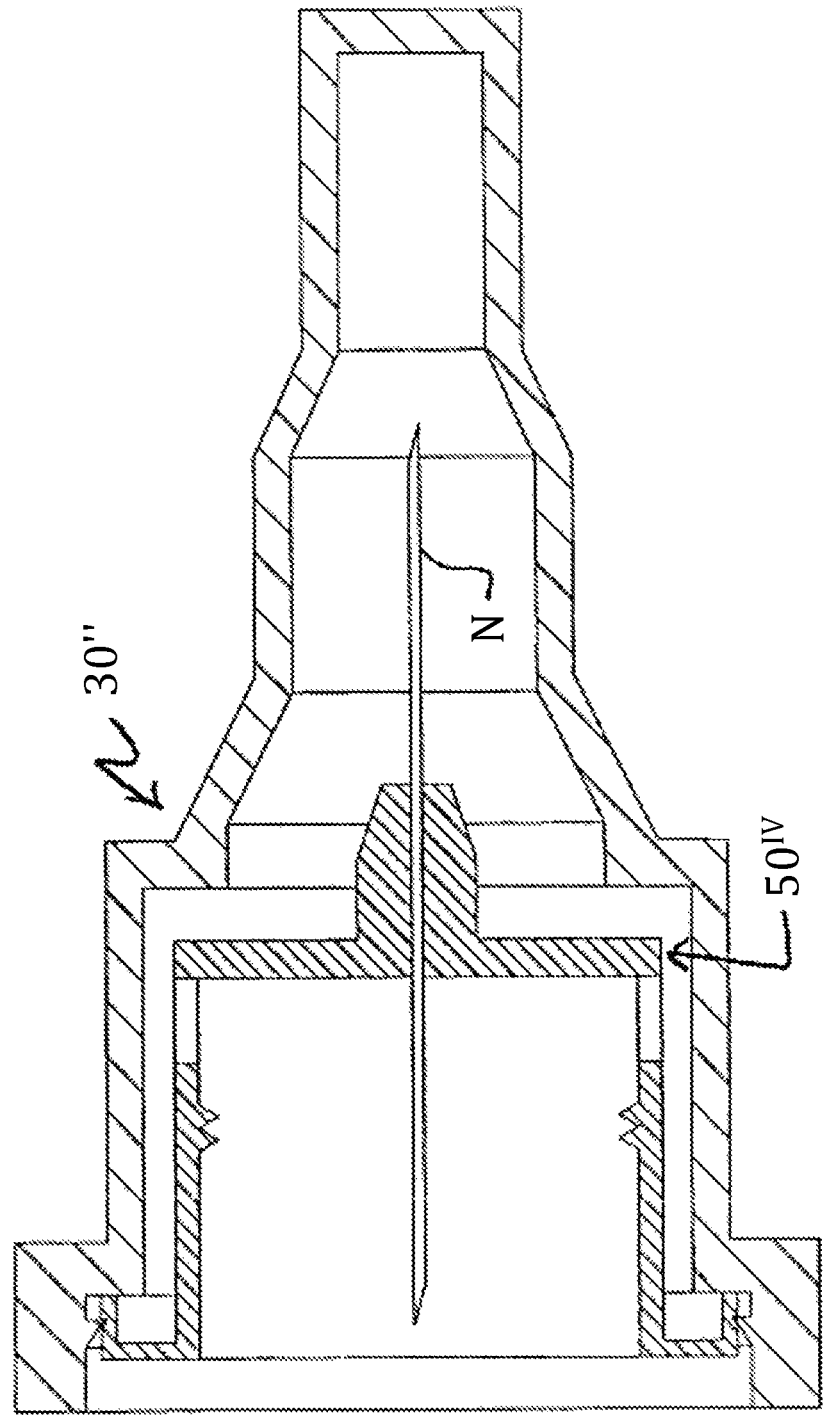
FIG. 19 shows a needle tip assembly of FIG. 18 with the needle cover removed and illustrates that, in this condition, the outer cover is locked to the needle tip or body. This condition would typically occur when the outer cover is fully re-installed and after injection. For clarity, the pre-loaded syringe is not shown.
Figure 20:
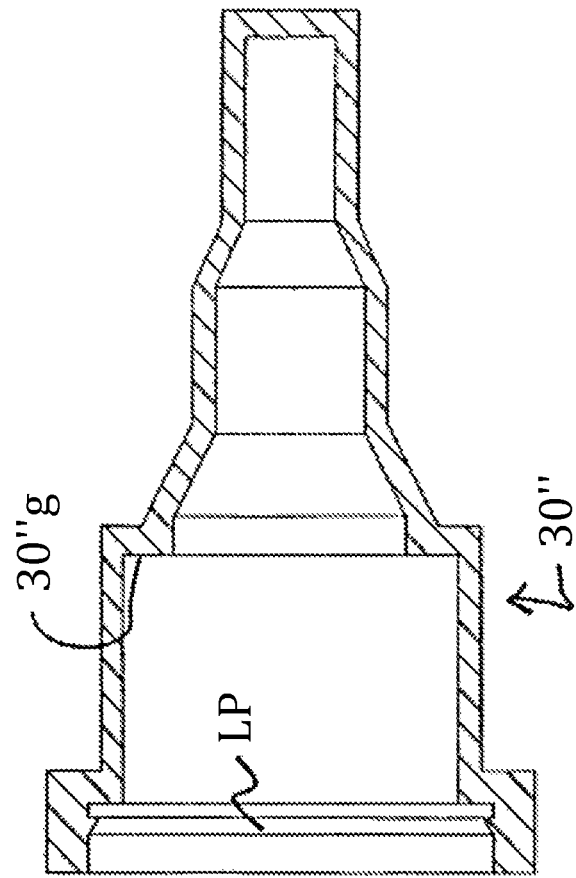
FIGS. 20 and 21 show end and side cross-section views of the outer cover utilized in the embodiment shown in FIG. 19.
Figure 21:
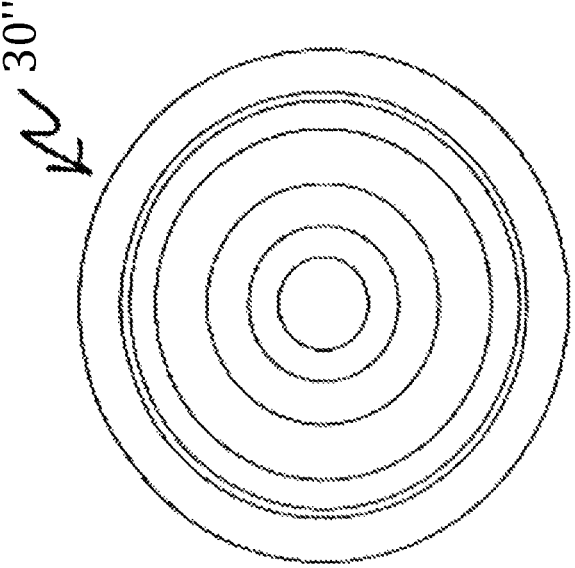

FIGS. 18-21 show another non-limiting embodiment of a pen needle assembly which utilizes a pen needle $50^{IV}$ that can be non-releasably locked to the packing cover 30" during removal. Again, although not shown in FIGS. 18 and 19, this embodiment can utilize a packaging seal member having a pull-tab similar to that shown in FIG. 1. An exemplary condition by which the non-limiting embodiment shown in FIGS. 18-21 may be installed or removed will now be discussed. Under an installation condition, a user merely slides the pen needle $50^{IV}$ onto the section 2 by gripping the packing body 30" while the needle cap 40' is installed on the hub with end 40'a covering the needle (as shown in FIG. 18). During installation, an annular surface 30"g of the packing body 30" exerts a force on the flange 40'b while the flange 40'b abuts the pen needle $50^{IV}$. The flange 40'b has sufficient thickness to prevent the pen needle $50^{IV}$ from locking to the outer cover 30", i.e., this thickness prevents the pen needle $50^{IV}$ and cover 30" from moving with respect to each other to a position where the locking recess LR engages with the locking projection LP. With the configuration shown in FIG. 18, the pen needle $50^{IV}$ can be fully installed (either by sliding on or by rotating and threading on) onto the section 2 with the teeth engaging with the thread of the section 2. However, as noted above, as long as the needle cap 40' remains installed as shown in FIG. 18, the pen needle $50^{IV}$ cannot, during the installation, become (or is prevented from being) locked to the packaging body 30". Prior to injection, of course, the needle cap 40' is removed, and can even be discarded. After an injection and while the pen needle $50^{IV}$ remains installed on the section 2 (not shown in FIG. 19), a user can remove the pen needle $50^{IV}$ by re-installing the packing body 30" (without the needle cap 40'). As should be apparent from FIG. 19, the user slides on the packing body 30" fully over the installed pen needle $50^{IV}$ until the pen needle $50^{IV}$ assumes the non-releasably locked position shown in FIG. 19. Locking occurs when the projection LP engages with the recess LR. At this point, the user can pull the pen needle $50^{IV}$ off of the section 2 and discard the same. With the pen needle $50^{IV}$ in the non-releasably locked position shown in FIG. 19, it can be either slid off or unthread from the section 2. Although rotation is not required for removal because the elements having the teeth can deflect outwardly, an unthreading rotation movement may be preferred because the teeth of the pen needle $50^{IV}$ remain (when installed) in frictional engagement with the threaded section 2 of the injection device 1. Moreover, when the pen needle $50^{IV}$ is removed from the section 2, it is safely positioned inside the cover or packaging body 30'''—which has functioned, in addition to packaging, as a removal tool, a re-use prevention device, and a safety shield. Disposal of the assembly shown in FIG. 19 can now more safely occur, i.e., during handling, the user and others are prevented by the cover 30" from being punctured by the needle N.

Figure 22:
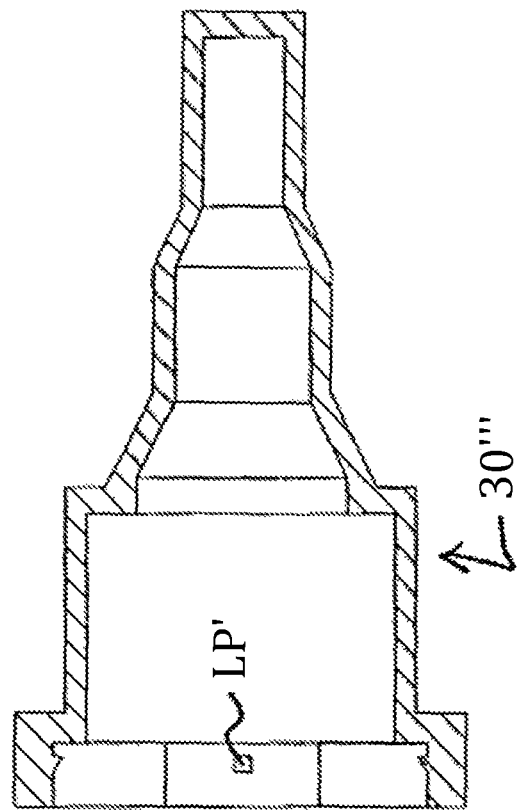
FIGS. 22 and 23 show end and side cross-section views of another embodiment of an outer cover that can be utilized in the invention.
Figure 23:
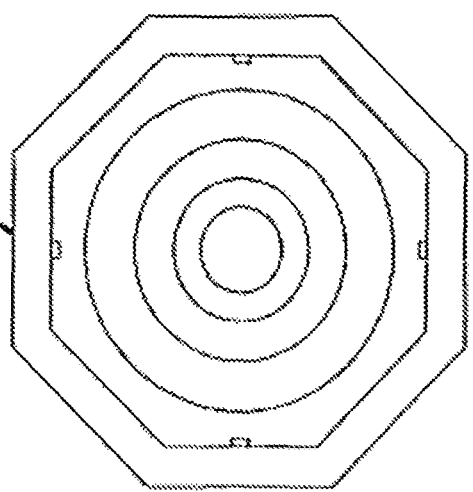

FIGS. 22 and 23 show end and side cross-section views of an embodiment of an outer cover 30''' that can be utilized in the invention. This embodiment differs from that of FIGS. 20 and 21 in that a distal or rear end portion 30'''b has a polygonal shape, i.e., hexagonal. In addition, instead of one or more locking projections being arranged on an inner circular or cylindrical surface, the one or more locking projections LP' are arranged on inner surfaces of one of more sides of the hexagonal shaped rear end 30'''b. An exemplary pen needle $50^V$ which can be used with the cover 30' is shown in FIGS. 22 and 23. One or more locking recess LR' is arranged on the polygonal shaped flange $57^V$.

Example 1

A needle tip assembly for a pre-loaded syringe or a pen needle injection device can be of the type shown in FIGS. 10-12, wherein the needle tip assembly or pen needle 50' comprises a double-ended needle N and is installable and removable from the pre-loaded syringe or pen needle injection device 1. A needle cap 40 is configured to cover a skin puncturing end of the double-ended needle N and is removable to expose the skin puncturing end. An outer cover 30 structured and arranged to at least install the pen needle 50 onto the pre-loaded syringe or pen needle injection device and remove the same from the pre-loaded syringe or pen needle injection device after the outer cover 30 is re-installed. The pen needle 50' is lockable to the outer cover 30 upon either of re-installation of the outer cover 30 (FIG. 11) and/or prior to the pen needle 50' being removed from the pre-loaded syringe or pen needle injection device 1.

The pen needle device or assembly shown and described above or herein can also utilize one or more features disclosed in the prior art documents expressly incorporated by reference herein. Furthermore, one or more of the various parts or components of the assembly can preferably be made as one-piece structures by e.g., injection molding, when doing so reduces costs of manufacture. Non-limiting materials for most of the parts include synthetic resins such as those approved for syringes or other medical devices. Furthermore, the invention also contemplates that any or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A needle tip assembly for a pre-loaded syringe or pen needle injection device, the needle tip assembly comprising:
   a body comprising a double-ended needle and being installable and removable from the pre-loaded syringe or pen needle injection device, wherein the body comprises outwardly deflectable teeth engageable with threads on the pre-loaded syringe or pen needle injection device;
   a needle cap configured to cover a skin puncturing end of the double-ended needle and being removable to expose the skin-puncturing end; and
   an outer cover structured and arranged to at least:
      install onto the body of the needle-tip assembly device;
      be re-installable and non-releasably locked to the body while the body remains installed on the pre-loaded syringe or pen needle injection device, wherein, when the outer cover is re-installed to the body, the outwardly deflectable teeth outwardly deflect to disengage the outwardly deflectable teeth from the threads; and
      remove the body from the pre-loaded syringe or pen needle injection device after the outer cover is re-installed to the body;
   wherein, after re-installation of the outer cover and removal of the body from the pre-loaded syringe or pen needle injection device, the double-ended needle is positioned inside the outer cover without use of the needle cap, thereby preventing puncturing by a user of the double-ended needle.

2. The needle tip assembly of claim 1, wherein the outer cover is structured and arranged to contain therein the body and the needle cap in a prior use and sterile package condition.

3. The needle tip assembly of claim 1, wherein the body is a one-piece body.

4. The needle tip assembly of claim 1, wherein the outer cover is a one-piece body.

5. The needle tip assembly of claim 1, wherein the needle cap is a one-piece body.

6. The needle tip assembly of claim 1, wherein the outer cover has an axial length that is greater than an axial length of the body and a closed front end.

7. The needle tip assembly of claim 1, wherein the outer cover has an axial length that is greater than an axial length of the needle cap.

8. The needle tip assembly of claim 1, wherein installation of the needle tip assembly to the pre-loaded syringe or pen needle injection device is by sliding.

9. The needle tip assembly of claim 1, wherein removal of the body from the pre-loaded syringe or pen needle injection device is by sliding off or by unthreading of the body from the pre-loaded syringe or pen needle injection device.

10. The needle tip assembly of claim 1, wherein the outer cover has a visual indicator to a user that a needle is disposed within the outer cover, has been used, and should not be used again.

* * * * *